(12) United States Patent
Howells et al.

(10) Patent No.: US 8,975,085 B2
(45) Date of Patent: Mar. 10, 2015

(54) EXTRACTION SYSTEM

(75) Inventors: Jonathan Spencer Howells, Herts (GB); Kevin Deane, Cambridge (GB)

(73) Assignee: PA Knowledege Limited, London (GB)

( * ) Notice: Subject to any disclaimer, the term of this patent is extended or adjusted under 35 U.S.C. 154(b) by 1009 days.

(21) Appl. No.: 13/058,828

(22) PCT Filed: Aug. 6, 2009

(86) PCT No.: PCT/GB2009/001947
§ 371 (c)(1),
(2), (4) Date: May 4, 2011

(87) PCT Pub. No.: WO2010/020752
PCT Pub. Date: Feb. 25, 2010

(65) Prior Publication Data
US 2011/0212539 A1 Sep. 1, 2011

(30) Foreign Application Priority Data

Aug. 18, 2008 (GB) .................................. 0815093.0

(51) Int. Cl.
*G01N 1/38* (2006.01)
*G01N 1/40* (2006.01)
(Continued)

(52) U.S. Cl.
CPC ................ *B01F 1/0027* (2013.01); *G01N 1/38* (2013.01); *B01F 1/0038* (2013.01); *B01F 5/10* (2013.01); *B01F 11/0266* (2013.01);
(Continued)

(58) Field of Classification Search
CPC .............. G01N 2013/006; G01N 2035/00198; B01F 2001/0055; B01F 2001/0061
See application file for complete search history.

(56) References Cited

U.S. PATENT DOCUMENTS 3,620,675 A  11/1971  Olson
4,247,298 A   1/1981  Ripple
(Continued)

FOREIGN PATENT DOCUMENTS

DE  9 35 726       11/1955
DE  39 22 299 C1   4/1991
(Continued)

OTHER PUBLICATIONS

Stroock, Abraham D. and George M. Whitesides. "Controlling flows in microchannels with patterned surface charge and topography." Accounts of Chemical Research (2003) 36 597-604.*
(Continued)

*Primary Examiner* — Christopher A Hixson
(74) *Attorney, Agent, or Firm* — Foley & Lardner LLP (57) ABSTRACT

An extraction system for distributing a test product in an extraction fluid, the system including a flow cell and a pump The flow cell has walls defining an internal passageway having an extraction region for holding the test product and also an upstream end and a downstream end between which the extraction region extends. The internal cross-sectional area of the upstream end is larger than the internal cross-sectional area of the downstream end the and extraction region tapers from the upstream end to the downstream end. The pump has an inlet in fluid communication with the downstream end and an outlet in fluid communication with the upstream end. The pump re-circulates extraction fluid from the downstream end back to the upstream end so as to progressively erode the test product and distribute the test product in the extraction fluid.

25 Claims, 6 Drawing Sheets

(51) Int. Cl.
  *B01F 1/00* (2006.01)
  *B01F 5/10* (2006.01)
  *B01F 11/02* (2006.01)
  *B01F 15/04* (2006.01)
  *B01F 15/00* (2006.01)
  *G01N 35/00* (2006.01)

(52) U.S. Cl.
  CPC ........ *B01F 11/0283* (2013.01); *B01F 15/0437* (2013.01); *G01N 1/4055* (2013.01); *G01N 2001/383* (2013.01); *B01F 15/00123* (2013.01); *B01F 2001/0061* (2013.01); *G01N 2001/4061* (2013.01); *G01N 2035/00554* (2013.01)
  USPC ........................................................ 436/174

(56) References Cited

U.S. PATENT DOCUMENTS

| | | | |
|---|---|---|---|
| 5,439,288 A | | 8/1995 | Hoffman et al. |
| 5,511,875 A | * | 4/1996 | Jonsson et al. ................ 366/136 |
| 5,750,008 A | | 5/1998 | Lautenschlager |
| 5,833,867 A | * | 11/1998 | Hensley ........................ 210/792 |
| 2003/0124204 A1 | | 7/2003 | Sweet |
| 2004/0016442 A1 | | 1/2004 | Cawlfield |

FOREIGN PATENT DOCUMENTS

| | | |
|---|---|---|
| DE | 39 22 299 C1 | 4/1991 |
| EP | 1 152 081 A1 | 11/2001 |
| EP | 1 167 946 A2 | 1/2002 |
| EP | 1 167 946 B1 | 8/2008 |
| WO | WO-90/07975 | 7/1990 |
| WO | WO 90/07975 | 7/1990 |
| WO | WO-03/066203 A1 | 8/2003 |

OTHER PUBLICATIONS

Communication and Partial European Search Report EP 13 15 0291 dated May 22, 2013.

International Search Report in PCT/GB2009/001947 dated Dec. 1, 2009.

Search Report in GB Appln No. 0815093.0 dated Dec. 17, 2008.

* cited by examiner

EXTRACTION SYSTEM

The present invention relates to a rapid extraction system for distributing a test product in an extraction fluid.

It is known to take a solid product, such as a pharmaceutical product, for testing and to distribute that product in an extraction fluid, for instance by dissolving that product or providing that product in suspension, for subsequent testing. It is known to do this by using trained analytical chemists working in laboratories using traditional volumetric glassware. The glassware is typically flasks and pipettes calibrated at the highest class of quality available.

A pharmaceutical product, such as a tablet, is added to a glass volumetric flask which is then part filled with the extraction liquid. The flask is gently shaken or stirred or placed in an ultrasonic bath to break up the tablet. This process is known as product extraction step and is the major bottleneck in the overall testing process. The reason for the low productivity of the test process is that the volumetric flasks are fragile and can not be used in vigorous mixing processes. Therefore the existing method is low energy and consequently a slow extraction method. This extraction step can take anything from several minutes to many hours depending on the product. The flasks are checked frequently by analytical chemists, as the process can be variable. The flasks are then made to volume with more extraction liquid and finally filtered to obtain a clear solution. Normally, the filtrate is accurately diluted using more flasks and pipettes. It may then be tested with an appropriate analysis technique, for instance using high-performance liquid chromatography (HPLC).

The process is very time-consuming and subject to variability. Overall laboratory sample preparation is a known bottleneck and manual preparation is subject to human errors, with many atypical results and subsequent costly investigations.

Some automated solutions have been proposed. However, these are vessel-based and use robotics having highly intrusive extraction devices to break up the products.

The present application contemplates extraction for broad product types such as foods, materials, minerals, etc as well as pharmaceuticals. It contemplates getting from a sample, which might be solid, to a liquid extract for analysis.

It is an objective of the present invention at least to reduce the problems mentioned above.

According to the present invention, there is provided a method of distributing a test product in an extraction fluid, the method including:

providing a flow cell having walls defining an internal passageway having an extraction region for holding the test product and having an upstream end and a downstream end between which the extraction region extends;

locating the test product in the extraction region;

driving a fluid through the flow cell from the upstream end to the downstream end so as to progressively erode the test product; and recirculating the extraction fluid from the downstream end back to the upstream end so as to distribute the test product in the extraction fluid as it is progressively eroded.

By driving the fluid through the flow cell in this way, it is possible to create vigorous turbulence.

According to the present invention, there is provided an extraction system for distributing a test product in an extraction fluid, the system including:

a flow cell having walls defining an internal passageway having an extraction region for holding the test product and having an upstream end and a downstream end between which the extraction region extends; and a pump having an inlet in fluid communication with the downstream end and an outlet in fluid communication with the upstream end, the pump being configured to re-circulate extraction fluid from the downstream end and back to the upstream end so as to progressively erode the test product and distribute the test product in the extraction fluid.

In this way, the test product is effectively broken up and eroded and distributed in the recirculating extraction fluid. Recirculation of the extraction fluid ensures that the test product becomes fully distributed in the extraction fluid. The resulting extraction fluid is then easily available for analysis.

The internal passageway may be provided with features to promote rapid flow, turbulence and prevent blockages.

The present invention utilises a process to continuously re-circulate the extraction solvent in a closed loop, achieving multiple passes through the product which is held in a sample holding vessel somewhere in the fluid path. Recirculation is described in prior art for various flow cells for the purpose of dissolving a variety of solutes from solid matrixes in a continuous flowing manner. This continuous recirculation process provides efficiencies by continuously recycling the initial aliquot of solvent added into the loop without needing to add fresh solvent. The benefits gained are from unattended operation without manual intervention and the process can be left for long periods of time gradually building up the concentration of the solute. However, for laboratories testing purposes rapid extraction is required to increase productivity. Product extraction needs to be complete within several minutes to deliver any benefit to product testing.

Research has shown that to achieve rapid tablet extraction very high flow rate is required to rush past the surface of the product to strip away at the layers of the formulation. The greater the turbulence in the flow the more aggressive is the effect and at very high flow rates even the hardest components of the products erode quickly. The research has also shown that any insoluble materials released from the disintegrating products acts like sand blasting which further increases the rate of product extraction.

Re-circulation systems can work well at low flow rates but are likely to block at high flow rates with potentially disastrous consequences. For the reasons described below the prior art can not work for rapid extraction and new features are required to overcome the following problems:

A percolation extraction process as described in US 2003/0124204 A1 that utilises a closed loop recycling of liquid in a flow cell containing a bed of powder will not allow sufficient flow to achieve any rapid extraction. Percolation is a process best suited to low pressure and low flow rates, allowing time for slow diffusion of solutes from a matrix. Increasing the flow rate will lead to problems of high pressure and blockages. Additional features in the flow cell are required to prevent this problem.

A controlled laminar flow process as described in U.S. Pat. No. 5,439,288 for particle sizing does not provide optimum conditions for rapid extraction where research has shown that rapid turbulent flow is required. The ultrasonic flow-cell described needs to be re-designed to hold a test product and have additional features to promote turbulence and prevent blockages at high flow rates.

A process based on a cyclone as described in EP 1 152 081 A1 achieves a controlled swirling of solvent that is substantially laminar and would not work efficiently if partially blocked by a tablet, which can be of substantial size. Cyclones work well for particle sizing but offer no advantages for rapid extraction.

A low pressure extraction process in a flow cell as described in PCT/DK90/00015 intended for extraction from a resin bed for the purpose of chemical synthesis is preferred to have a flow that is substantially laminar to prevent risk of mechanical collapse of the bed. This type of invention can not work well when the flow rate of re-circulating liquid is high as it does not promote turbulence and aggressive extraction conditions.

The present invention describes the application of a rapid extraction flow cell with novel features that is aimed at overcoming the issues described above in existing prior art to make it work for rapid extraction purposes.

Novel following features in the flow cell are required to stimulate the following conditions:

1. High solvent flow rates, where the present invention has a defined geometry in the sample holding vessel to accelerate liquid past the product, by restricting the outlet to create a large pressure differential in the cell. This achieves very high liquid flow in the cell whilst enabling the rest of the fluid circuit to operate at lower flow rates achievable by a peristaltic pump, desirable for this application. The geometry of the cell is substantially a cone shape which is keeps the product in contact with the accelerating liquid for as long as possible. As the product erodes it slides further down the cone experiencing ever faster fluid rates and consequently faster extraction rate 2. Turbulence in the cell, where the present invention has additional features added to the sample holding vessel to create additional turbulence or aggressive eddies in the flow around the tablet. In this present invention this is achieved by having grooves in the cone surface to create complex pathways for the rushing liquid.

3. Additional features in the exit of the sample holding vessel to prevent blockages from occurring as the product disintegrates by providing passages to keep the flow rate high. In the present invention this is achieved by defining features in the exit hole that retain larger particles, but create alternative avenues for the flowing liquid and prevent blockages.

4. Additional features to retain disintegrating smaller particles or beads in the cone for as long as possible so as to experience the fluid at its highest flow rate. In the present invention this is achieved by having a wire or mesh or coarse filter material near or at the exit hole to trap particles or beads without attenuating the of flow rate of liquid.

It would be possible to provide the extraction region with a cylindrical shape. However, preferably, the upstream end has an internal cross-sectional area, the downstream end has an internal cross-sectional area, the internal cross-sectional area of the upstream end being larger than the internal cross-sectional area of the downstream end and the extraction region tapering from the upstream end to the downstream end.

The shape of the flow cell is advantageous in breaking up the test product.

Although a number of different tapering cross-sections would be effective in carrying out the present invention, typically the extraction region is substantially conical, either with stepped or smooth sides.

Preferably, the included angle of the conical extraction region is substantially 55°.

Similar angles will be equally effective for other product shapes of tapered extraction region. Angles are possible between 40° and 70°, or more preferably, 50° and 60°.

Preferably, for the extraction region, the walls defining the internal passageway have a shape defining a plurality of grooves side by side around the internal passageway, each one of the grooves extending at least partly from the upstream end to the downstream end.

The grooves are very effective in allowing the extraction fluid to continue flowing and create additional powerful turbulence that increases extraction rate. They can inhibit the test product from blocking up the extraction region. Also, the grooves can be effective in creating turbulence and vortices which assist in breaking up the test product.

A single set/plurality of grooves can be provided along the entire length of the extraction region. However, preferably, adjacent to the upstream end, a first plurality of said grooves are provided and, adjacent the downstream end, a second plurality of said grooves are provided.

This allows different effects to be achieved at different portions along the length of the extraction region.

Preferably, the first plurality is greater than the second plurality.

In this way, similar sized grooves can be provided around the larger circumference adjacent the upstream end and a smaller number of grooves can be provided around the smaller circumference adjacent the downstream end.

It is possible for the first plurality to be approximately 10 and the second plurality to be approximately 4.

The sample holding vessel/flow cell can be of any volume and could be provided according to the needs of the user and the type of product to be tested. However, typically, for known pharmaceutical products, it is preferred that the flow cell has an internal volume between 5 ml and 100 ml.

This allows most pharmaceutical products of typical sizes to be held and distributed as required.

The internal cross-sectional area of the upstream end is preferably in the region of 500 mm$^2$. Where the extraction region is conical, this equates to a diameter of approximately 25 mm.

In this way, most typical pharmaceutical products can be inserted into the extraction region from the upstream end.

In contrast, for such an extraction region, the internal cross-sectional area of the downstream end is approximately 3 mm$^2$. This is advantageous in providing the desired increase in flow stream rate for erosion and break up of the test product.

In some arrangements, the orifice at the outlet end could be variable in size, in particular narrowing to increase liquid acceleration to get more vigorous extraction or widening if blocking occurs.

Preferably, at a position downstream of the upstream end, a mesh element is provided bridging the internal passageway so as to retain the test product.

As a test product is broken up, parts of the test product can become detached. However, it is preferable that these are retained in the extraction region as long as possible. The mesh can assist in retaining relatively small parts of the test product that have become detached.

The mesh element could be provided at or downstream of the downstream end of the extraction region. Alternatively, the mesh element could be provided at a position between the upstream end and the downstream end.

Where a first and a second plurality of grooves are provided in the extraction region, the mesh element can be provided at a position between those two sets of grooves.

This can be convenient in construction. In particular, the extraction region, having the two sets of grooves can be made from two components each including a respective set of grooves. The mesh element can then be positioned between these two components.

The mesh element may be constructed as a filter or just be a single wire.

For typical test products, it is proposed that a mesh with capacity to hold particles in the region of 0.3 mm in size is suitable.

The extraction fluid may be re-circulated either by sucking from the downstream end of the flow cell or by pumping into the upstream end of the flow cell.

It is advantageous for the system to be run under pressure. Hence, preferably, the flow cell and the pump are constructed so as to be connected and sealed so as to form a pressurized system.

The temperature of the extraction fluid can be controlled, for instance with higher temperatures for increased extraction rates. Temperatures between 10° C. and 70° C. are proposed.

In order to enhance further the break-up of the test product, the system may include an ultrasonic vibration generator. This is configured to introduce ultrasonic vibrations to the flow cell.

The ultrasonic vibrations may be advantageous in helping to break up the test product.

The ultrasonic vibration can be supplied internally (for instance using a sonotrode) or externally through the walls of the flow cell.

In one preferred embodiment, the system further includes an outlet valve providing fluid communication between the downstream end and selectively one of the inlet of the pump and a collection port from which fluid from the system can be collected.

In this way, once the test product has been fully distributed in the extraction fluid, the valve can connect the downstream end of the extraction region to the collection port so that the extraction fluid can be collected.

Preferably, a filter is provided upstream of the collection port so as to provide a filtrate of the extraction fluid at the collection port.

A meter may be provided downstream of the downstream end. This may be configured to measure properties of the extraction fluid flowing from the downstream end and to output a corresponding signal.

The meter preferably provides information indicating when the test product has been fully distributed throughout the extraction fluid.

The meter could include one that can measure no-specific absorption (e.g. turbidity meter) or one that can sense specific absorption for example a probe for UV (Ultra-Violet Spectrophotometric), IR (Infra Red) or NIR (Near Infra Red).

The system preferably includes a controller configured to control the pump to pump extraction fluid under pressure from the downstream end to the upstream end so as to re-circulate the extraction fluid.

The controller may also be configured to analyse the signal output from the meter and to determine from the analysis when the test product is fully distributed in the extraction fluid.

In this way, the system may be fully automated. In particular, the controller may be configured to slow the pump and control the outlet valve to connect the downstream end to the collection port when it is determined that the test product is fully distributed in the extraction fluid.

The controller is preferably able to determine when blockages occur in the system. This determination may be achieved by monitoring the performance of the pump and/or information obtained from the meter.

Hence, preferably, the controller is further configured to reverse the direction of pumping of the pump when a blockage is determined.

In this way, the system is able easily to remove blockages.

It is also possible to include a moveable pin that rises upwards to unblock the exit.

Where an outlet end of variable size is provided, this may be controlled in response to sensed blockages.

The invention will be more clearly understood from the following description, given by way of example only, with reference to the accompanying drawings, in which.

There is described herein an improved system for use for sample preparation for drug content of pharmaceutical products. Other similar systems can be used for extraction with other product types such as foods, materials, minerals, etc.

With the present invention, it becomes possible to automate the task of sample preparation. This can be closely integrated to a test instrument, such as used to perform High Performance Liquid Chromatography (HPLC). The invention may be embodied as a simple process that can be made reliable and repeatable. Embodiments may be derived which are scaled as compact scientific instruments, rather than large robotic devices, and are suitable for use in laboratories. In particular, by virtue of the present invention, it is not necessary to use intrusive mechanical devices, such as homogenisers to break up tablets as has been proposed previously. Also, the cleaning cycle may be made quicker.

As will be apparent from the following description, it also becomes possible to integrate embodiments of the invention with HPLC, thereby giving analysts new tools that complement the way that they work and bring greater productivity and better quality.

Figure 1:
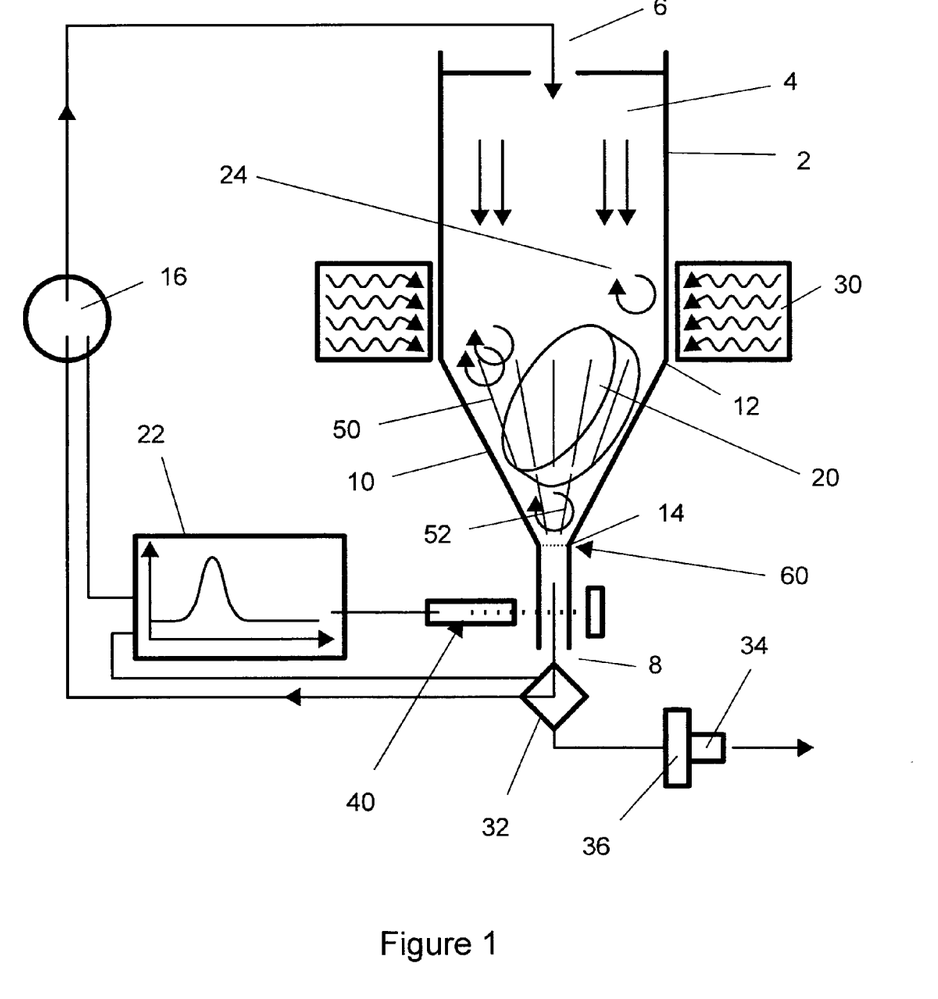
FIG. 1 illustrates schematically a system embodying the present invention.

A system embodying the present invention is illustrated schematically in FIG. 1 of the accompanying drawings.

The system includes a flow cell (2) which defines an internal passageway (4) leading from a fluid inlet (6) to a fluid outlet (8).

Between the fluid inlet (6) and the fluid outlet (8), there is an extraction region (10) having an upstream end (12) and a downstream end (14).

Extraction fluid, for instance extraction liquid of any known type, is able to pass through the flow cell (2) from the fluid inlet (6), through the extraction region via the upstream end (12) and downstream end (14) and out of the fluid outlet (8). As illustrated schematically in FIG. 1, this fluid can then be pumped, by means of pump (16), back to the fluid inlet (6) so as to re-circulate the extraction fluid around the system. Preferably, the extraction fluid is pumped under high pressure.

In use, a test product (20), such as a tablet or a plurality of beads, is inserted in the flow cell (2) and then a controller (22) controls the pump (16) to re-circulate extraction fluid through the flow cell (2) until the test product (20) has been fully broken up or dissolved and distributed throughout the extraction fluid, for instance in solution or as a suspension.

The extraction fluid can be recycled either by being sucked out of the cell or pumped through, depending upon where the pump is located in the cycle. For an unsealed system, sucking can only achieve pressures up to 1 bar, whereas positive pumping at the inlet end can achieve much higher pressures.

The flow cell could be completely or only partially filled with extraction fluid provided that there is sufficient liquid present to couple with any ultrasonic vibration which might be being used.

Preferably, with only partial fill, if extraction fluid is pumped through the inlet, a powerful fluid jet can be provided which helps erode a test product (20) and cut/blast it within the flow cell.

Preferred embodiments recirculate the extraction fluid with a flow rate in the region of 3 liters per minute. It will be appreciated that the rate of product extraction is related to flow rate and faster flow rates will increase the extraction rate.

It is possible to control the fluid temperature. Higher temperatures could be used to increase extraction rate and lower temperatures could be used for temperature-sensitive products, for instance which degrade in solution. Temperatures between 10° C. and 70° C. are envisaged.

The particular size of the flow cell (2) can be chosen according to the amount of test product (20), for instance the number of tablets, that are to be extracted simultaneously. Small flow cells can be provided for use with single products and might typically have an internal volume of 5 ml to 20 ml. Larger flow cells can accommodate multiple products and might typically have volumes of 20 ml to 100 ml.

The size of the upstream end (12) of the extraction region (10) is chosen according to the largest of the test products intended for use with the flow cell (2). For typical pharmaceutical dosages, it is envisaged that an upstream end (12) of approximately 25 mm in diameter would be sufficient, giving an internal cross-sectional area of approximately 500 mm$^2$.

As will be discussed in greater detail below, the downstream end (14) of the extraction region (10) has a smaller internal cross-sectional area. A typical downstream end having an internal cross-sectional area of 3 mm$^2$ is considered to give a suitable liquid flow rate. The downstream end (14) may be made variable in size, as well as the fluid outlet (8) if appropriate.

The flow cell (2) allows rapid extraction and also provides a non-invasive sample preparation technique that can transform a test product (20) with a solid matrix, such as pharmaceutical dosage forms or food material, into fully disintegrated, homogenous liquid or suspension for purposes of testing. The extraction fluid is caused to flow at high rate past the test product (20) so as to carry out the extraction process. No intrusive abrading device (such as a homogenizer) is needed. This greatly minimises cleaning and cross-contamination issues that are critical for purposes of accurate testing.

The rapid flowing extraction fluid which flows past the test product (20) creates aggressive flow conditions and turbulent eddy currents (24) as illustrated schematically in FIG. 1. The overall effect is to dissolve or abrade the test product (20) to achieve rapid extraction of the ingredients from the matrix and to achieve the dissolving of any soluble components. As a result of the tapering of the extraction region (10), as the test product (20) disintegrates and diminishes in size, it experiences a greater flow rate of liquid and faster disintegration.

The extraction liquid is constantly recycled from the downstream end (14) and fluid outlet (8) back to the fluid inlet (6) and upstream end (12). This ensures that complete mixing of soluble components is always achieved. Solid, insoluble material from the disintegrating products is also recycled and acts as an abrasive on the remaining product, further increasing the extraction rate.

In one embodiment, an ultrasonic generator (30) may also be provided so as to introduce ultrasonic vibration to the flow cell (2). This may be achieved by dry or wet coupling.

The ultrasonic vibrations help accelerate the extraction process.

Preferred embodiments use ultrasonic vibration in the region of 30 kHz.

The ultrasonic vibration can be supplied internally, for instance using a sonotrode, or externally through the walls of the flow cell. In order to supply the vibrations internally, a suitable device, such as a sonotrode, can be inserted through the inlet (6) or through a side of the flow cell (2). If there is room for fluid flow around it, it might be inserted through the outlet (8).

The illustrated embodiment also illustrates schematically a valve (32) which is operable to connect the downstream end (14) and fluid outlet (8) either to the inlet of the pump (16) or to a collection port (34). After the test product (20) has been fully distributed throughout the extraction fluid, the pump (16) can be slowed and the valve (32) operated to connect the downstream end (14) and fluid outlet (8) to the collection port (34) so that the extraction fluid can be passed on for further testing.

In the illustrated embodiment, the collection port (34) is also provided with a filter (36). This allows a turbid suspension to be turned into a clear filtrate suitable for product testing.

The illustrated embodiment is also provided with a meter (40) for detecting a predetermined property of the extraction fluid so as to help determine when the test product (20) has been fully distributed throughout the extraction fluid. Suitable meters include turbidity meters and UV spectrophotometer probes.

As illustrated schematically in FIG. 1, controller (22) receives a signal from the meter (40) and, based on that signal, can control the pump (16) and the valve (32).

The controller processes the signal and is looking for stable state to indicate that extraction is complete. This could be rising UV absorbance signal from the drug in solution that eventually plateaus, or rising turbidity from the undissolved sample components that eventually plateaus. When the plateau is reached, then it is evidence that the extraction process is complete and can be stopped. This can be overridden with set extraction times without using the measurement to stop the process, if required.

Thus, in essence, the system of FIG. 1 can be used as follows. A test product (20), such as one or more tablets, capsules, or beads is located in the extraction region (10) of the flow cell (2). Extraction liquid (quantitive, volumetric or gravimetric) is then added and recirculated by means of the pump (16). Powerful vortices (24) strip material from the sides of the test product (20) and as the test product (20) diminishes in size, it slips further down the tapered extraction region (10). Ultrasonic vibrations transmitted from the vibration generator (30) transmitted via the extraction fluid can be used to help abrade the test product (20). The extraction fluid and disintegrated parts of the test product (20) are recycled back into the flow cell in a continuous loop so as to become thoroughly mixed. The meter (40) can be used to monitor the extraction progress. Once the controller (22) has determined that extraction is complete, it slows the pump (16) and controls the valve (32) to provide a clear filtrate at the collection port (34).

Of course, in many instances, full mixing can be guaranteed after a predetermined time such that it is not necessary to use the meter (40). Similarly, it would be possible for a user to control the pump (16) manually, rather than use the controller (22). The arrangement has the benefit of being simple in construction and being able to use low-cost components with almost no moving parts. In contrast to prior art techniques for extraction, the liquid is moved, rather than the vessels. As explained above, it is possible to incorporate a variety of sensing techniques to operate the closed-loop system.

It is possible that broken up parts of the test product (20) can cause blockages in the fluid communication of the system. However, the system allows fluid flow to be reversed easily any number of times, merely by reversing the direction of the pump (16). It is possible also for the meter (40) to detect such blockages or for the response of the pump (16) to indicate that there is a blockage. In either case, the controller (22) could be arranged automatically to reverse the flow of the fluid by means of reversing the direction of the pump (16) so as to clear the blockage.

As mentioned above, it is also possible for the orifice beneath the core to be variable in size, either to increase fluid acceleration to get more vigorous extraction or widen it if blocking is sensed. This may be programmable throughout and/or reactive to blockages.

It is also possible to provide an upwardly (as illustrated) moveable pin that rises up through the inlet (8) so as to unblock any blockages. This can be controlled similarly.

Figures 2, 4:
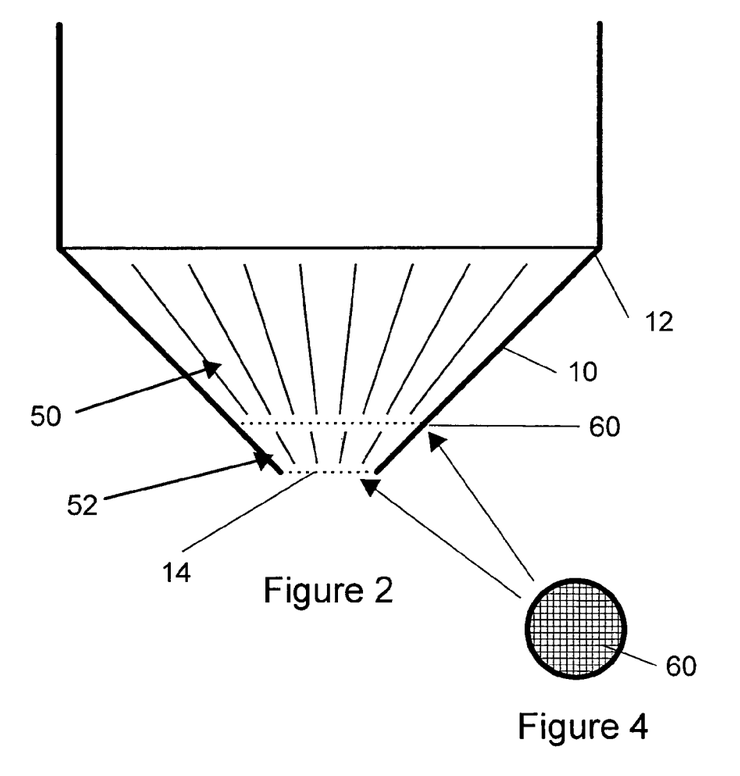
FIG. 2 illustrates schematically a preferred extraction region of the present invention.
FIG. 4 illustrates a mesh for the extraction region of FIG. 2.
Figure 3:
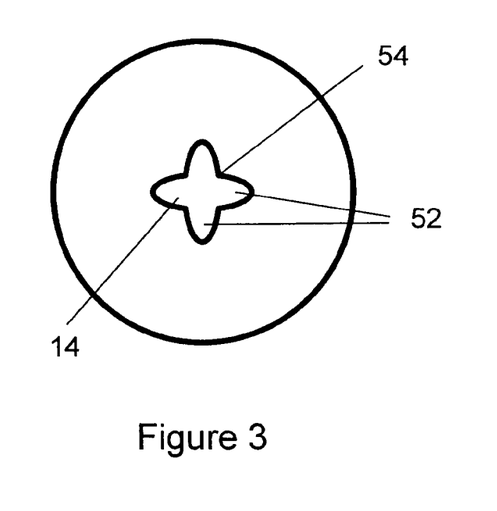
FIG. 3 illustrates schematically the downstream end of the extraction region of FIG. 2.

FIGS. 2 and 3 illustrate schematically, and not to scale, an embodiment of the extraction region of the present invention.

The extraction region is a means to hold the product in place to pump liquid past it and to expose it to ultrasonic vibration. To increase the flow, the extraction region includes internal sloping walls that narrow the internal cross-sectional area (diameter) down towards the downstream end (14). This causes an acceleration of the extraction fluid flow. The shape of the extraction region can be a simple cone with smooth sides or be stepped. In preferred embodiments, the walls defining the internal passageway have a more complex internal surface with slots or recesses to help locate the test products (20). Irrespective, for a cone-shape funnel, the included angle of the cone is preferably in the region of 55°.

FIG. 2 illustrates an extraction region (10) having a first plurality of grooves (50) adjacent the upstream end (12) and a second plurality of grooves (52) adjacent the downstream end (14). In a preferred embodiment, 10 grooves (50) may be provided around the periphery of the extraction region (10) adjacent the upstream end and four grooves (52) may be provided around the periphery of the extraction region (10) adjacent the downstream end (14). This enables a similar size of groove to be used at the narrower downstream portions of the extraction region despite the reduced circumference. It is possible for the extraction region (10) to be further divided into different portions along its axial length having different respective numbers of grooves. It is also possible for the same number of grooves to be provided along all of its axial length.

The grooves (50, 52) each at least partly extend in a direction from the upstream end (12) to the downstream end (14), in other words the axial direction of the tapered extraction region (10). In this respect, the grooves (50, 52) could be orientated straight down along the tapered surface or could be angled, for instance in a spiral pattern. This may increase the likelihood of contact with the test product (20).

In preferred embodiments, the grooves are typically in the region of 0.5 mm wide and 1 mm deep. The grooves extend down the internal surface of the funnel shaped extraction portion (10) from at least near the upstream end (12) of the extraction portion (10) towards the downstream end (14).

The grooves may have one or more of a mixture of profiles including parallel faces with flat bottoms, v-shapes or u-shapes.

The grooves are beneficial in creating additional escape routes for the liquid past the test product (20) so as to prevent unwanted pressure rises caused by blockages in the extraction portion (10) or downstream end (14). Also, the grooves (50, 52) can be used to increase extraction performance by providing additional localised routes of rushing liquid that flow vigorously past the test product (20) in contact with the extraction region (10).

Multiple grooves in the extraction region (for instance 1 to 10 have been shown to be effective) provide good coverage of the internal surface of the extraction region and provide greater chance of contact with the test product (20).

As illustrated in FIG. 3, the grooves (52) may extend right into the downstream end (14) giving indentations (52) in what would otherwise be a circular exit hole. The overall cross-sectional area of the hole is maintained at an area suitable to achieve the required restriction and flow rate (for instance 3 mm$^2$). However, the indentations to the otherwise circular exit hole create pinch points (54) which act to help trap larger particles of the test product (20) inside the flow cell (2) and retain them for longer.

It is also possible to provide a filter element (60), such as a mesh or an arrangement of thin wires to hold test product in place. Test product that is broken up might otherwise escape earlier than is desirable for good extraction.

The extraction region (10) may include the filter element (60) at its base near the downstream end (14), for instance as illustrated in FIG. 1. Alternatively, illustrated in FIG. 2, a mesh, such as illustrated in FIG. 4, may be positioned part way up the extraction region (10), for instance dividing the two regions of grooves (50, 52). With this arrangement, the extraction region (10) could be a two-part construction with the filter element (60) held at the join. Preferably, for retaining pharmaceutical beads, a mesh size in the region of 0.3 mm can be used.

The extraction region (10) of the flow cell (2) can be constructed in a variety of different ways. In some embodiments, the extraction region (10) can be provided as a permanent feature of the flow cell (2) and constructed of a material capable of withstanding high pressure. Such materials might include metal, for instance stainless steel 316, or suitable inert plastic materials that are resistant to the re-circulating liquids. Alternatively, the extraction unit (10) could be provided as a replaceable or interchangeable section. Such an arrangement allows minimization of the possibility of cross-contamination by creating a disposable or washable component. It also provides the option of changing the extraction region geometry to customize the flow cell (2) as required.

Embodiments are also possible where a completely removable fluid path, including the flow cell and tubing, is either discarded or recycled and therefore requires no cleaning.

Figure 5A:
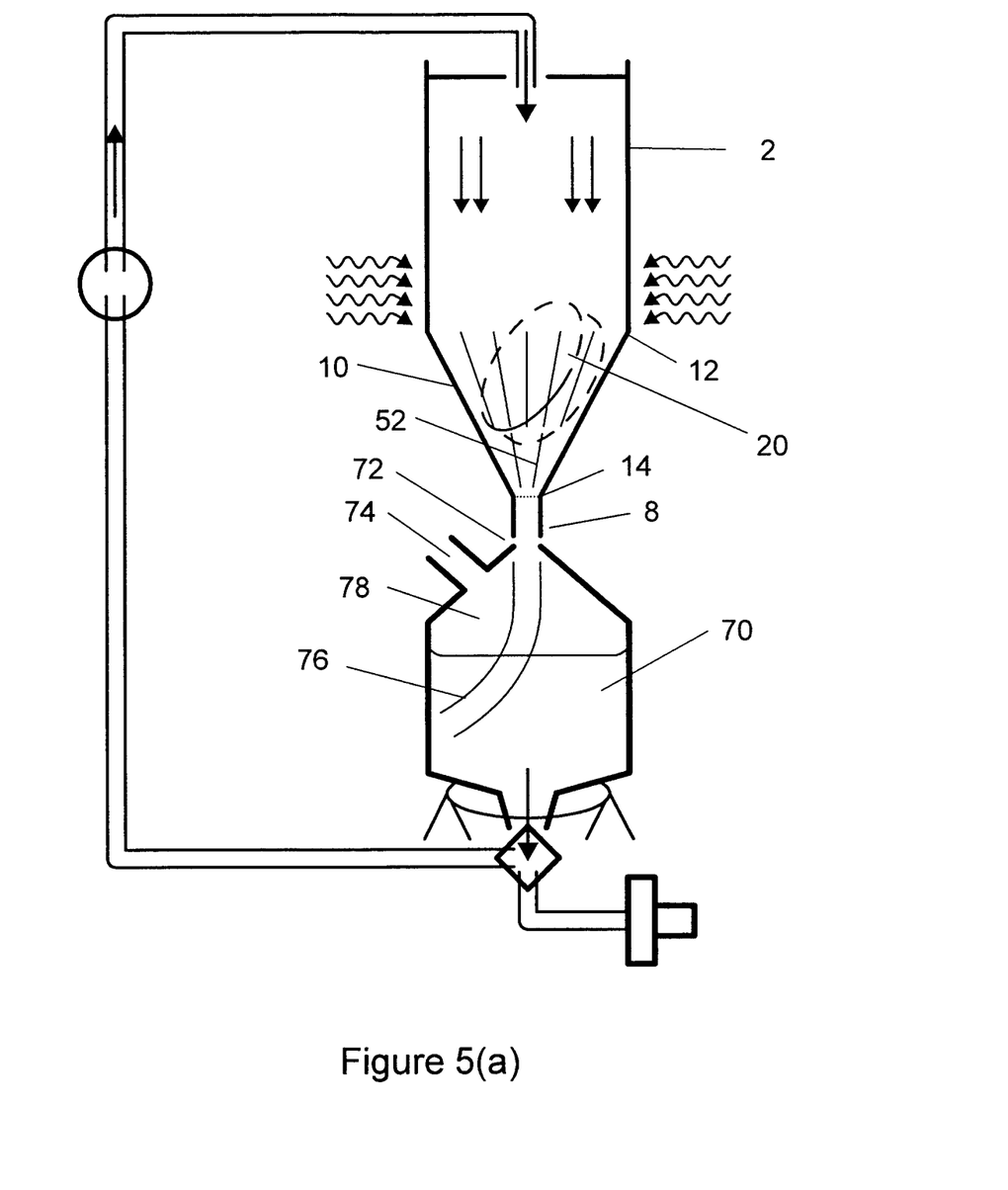
FIGS. 5(a) and (b) illustrate schematically an alternative embodiment of the system.

Embodiments are possible where a holding vessel is provided below the fluid outlet (8) of the flow cell (2). FIG. 5(a) illustrates this as a variation of the embodiment of FIG. 1.

The holding vessel (70) is provided to hold larger volumes of extraction fluid, for instance 250 ml. A coupling point (72) is provided for connection to the fluid outlet (8). The holding vessel (70) includes a port (74) into which additional extracting fluid may be provided and a passageway (76) such as a tube is provided to connect to the fluid outlet (8) of the flow cell (2) and to direct fluid below the level of fluid beneath an air space (78).

Figure 5B:
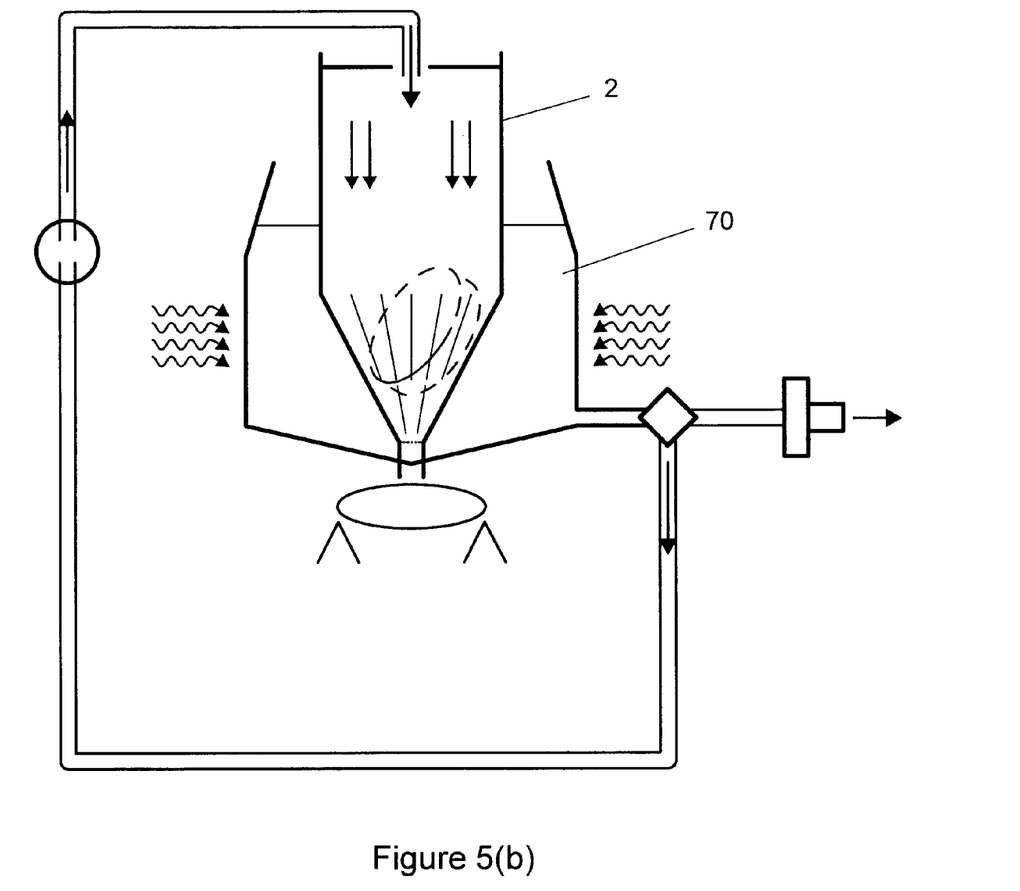

FIG. 5(b) illustrates a similar embodiment where the holding vessel (70) is arranged so as to surround the flow cell (2). The vessel (70) is filled with the accurate amount of extraction liquid and the flow cell (2) is immersed in the liquid. Ultrasonic vibration can be applied to the vessel (70) which couples through to the flow cell (2).

Either system may be provided with a downstream automatic dilution device which dilutes the fluid to achieve the correct concentration of desirable components for subsequent analysis. After the extraction process is complete, the fluid may be flushed away to waste and components of the fluid path can be washed, either using a remote washing machine for removable items or a clean-in-place system for permanent features.

Figure 6:
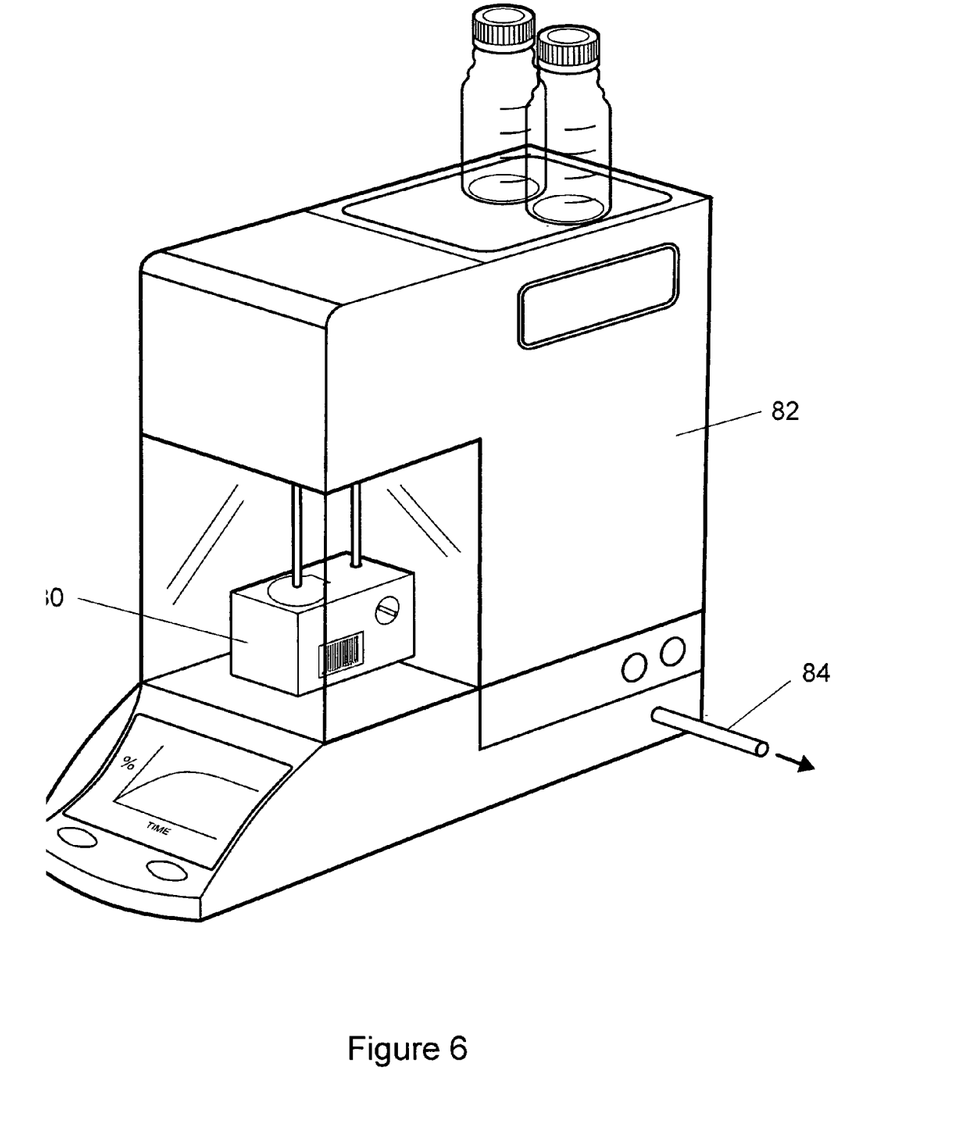
FIGS. 6 and 7 illustrate examples of implementations of systems of the present invention.

FIG. 6 illustrates schematically an embodiment including a removable cassette (80) for use with an extraction device (82). The removable cassette (80) includes the flow cell whereas the extraction device (82) provides the fluid path and extraction cycle.

A test product is provided in the flow cell of the cassette (80) and the cassette (80) is loaded into the extraction device (82). The extraction device (82) processes the cassette (80) and flow cell automatically. Preferably, it includes an autodiluter and vial handling to hold the final liquids. Alternatively, as illustrated, an outlet (84) can be provided for direct injection to the test instrument.

Dirty cassettes (80) can be removed when finished. Dirty cassettes can be discarded if disposable or, alternatively washed and then used again. The system is washed down (clean in place) and dried ready for the next test product waiting in the next cassette (80). During this cleaning time, the test instrument may process the sample which it was given, for instance taking five to twenty minutes.

In this way, one extraction device (82) can handle many test products, providing samples (just in time) for the test instrument. It is sufficient for a user to load up the samples of test product in cassette (80) at the beginning of the process and then leave the machine to process them automatically one at a time. In this regard, preferably, the extraction device (82) is provided with an appropriate form of conveying device for conveying successive cassettes (80) in place for the extraction process. Preferably, therefore, the extraction device (82) includes a CIP (clean-in-place system) and some form of autosampler for moving the cassettes and vials.

In a preferred embodiment, a plurality of cassettes (80) are provided with the same outer geometry for connection to the extraction device (82). However, those cassettes (80) may be provided with a variety of different flow cell geometries appropriate for different products. The extraction device can be a bench top system with a LCD display and control panel. A separate "wet" area is provided at the front with easy to clean surfaces. Working elements and electronics can be isolated at the back of the instrument. If desired, the front area can be a fully enclosed, guarded working area for providing safe operation. It may be provided with an automatic sliding door. Preferably, the working area is provided with transparent walls allowing viewing of operation. This may be confirmed by displaying sensor readings in real time on the LCD display. The cassette may be bar coded (or RFID coded) to provide tracking and link it to IT systems. A tray may be provided on the top surface for connection to appropriate extraction fluids.

Figure 7:
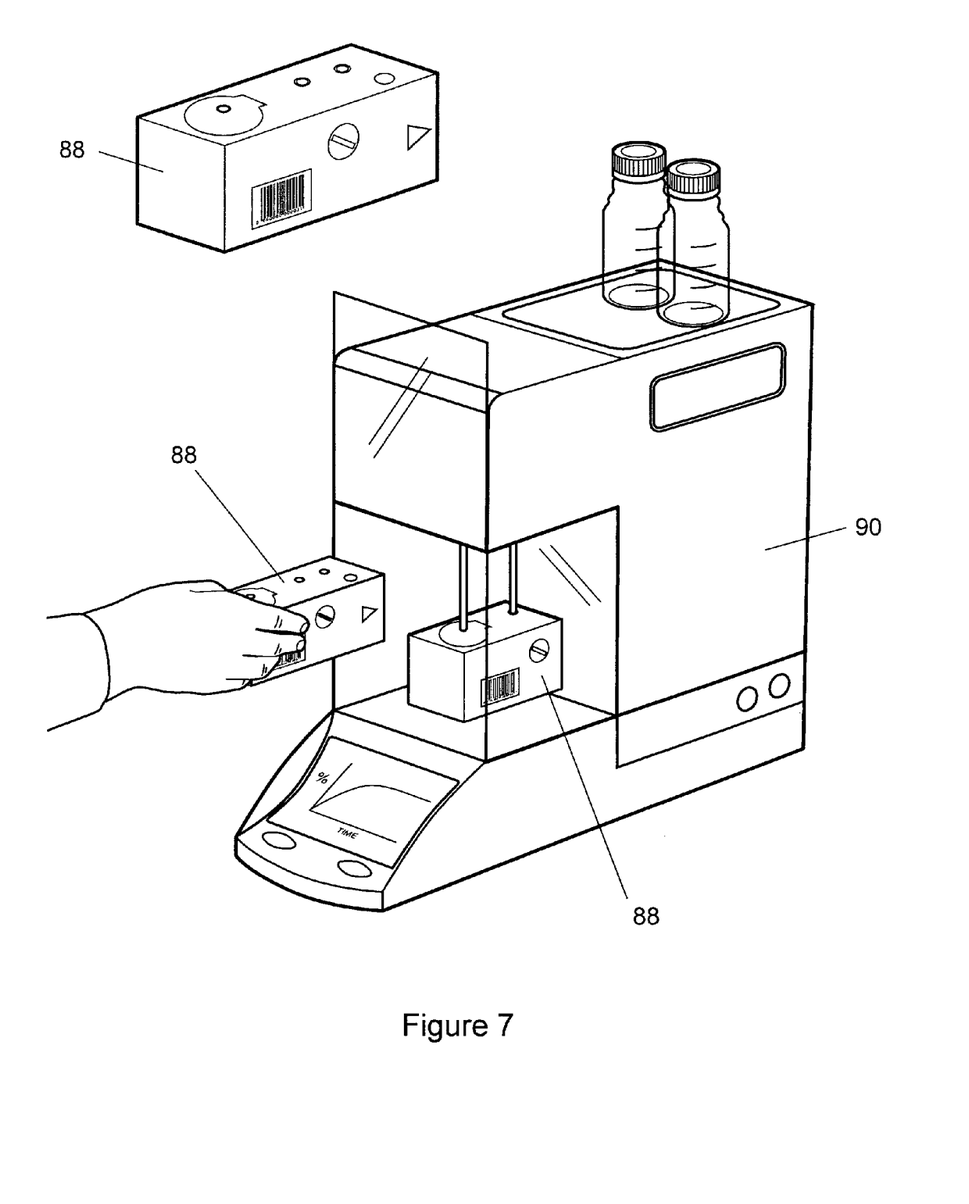

In another embodiment, a system may be provided that processes an individual sample using a removable cassette that is either disposable or washable for reuse. The removable cassette (88) can include a flow cell (2) containing the sample, filter and potentially a vial for output solution. The analyst adds the test product to the flow cell in the cassette and manually engages the cassette onto the extraction system. The system then automatically extracts the product and filters the liquid to produce the clear filtrate. The filtrate can then be collected in the vial in the cassette or pumped directly to either the test instrument for analysis or to autodilutor for further dilution. If a reusable cassette is used then it can either be emptied and cleaned manually by the analyst, or in a more complex embodiment of the system, automatically emptied and washed and dried in place using a CIP system. For the next sample the analyst can repeat the process with a new consumable or clean reusable cassette containing the next product for extraction. Such an extraction system could be used to extract multiple test products in parallel. The machines could be banked in any number in order to achieve the required throughput. This system is particularly useful when the analysis technique is rapid compared to the extraction process (e.g. a simple UV-Vis spectrophotometric assay). FIG. 7 illustrates schematically this embodiment of the present invention including a removable cassette (88) for use with an extraction device (90).

There are many benefits to the rapid extraction system.

It is possible to reduce the overheads in laboratory head count associated with routine analysis, thereby releasing highly trained staff for other value work. The extraction time to prepare a sample can be reduced to a minimum and samples can be prepared just in time for analysis. In this way, waiting time can be reduced for these instruments. By achieving better utilisation of the analytical instrument (such as HPLC), it is possible to reduce cycle times for results, keep the HPLC at higher equipment utilization, reduce the overall number of HPLC devices and realise the benefits of faster new generation HPLC devices (known as UPLC) and reduce the overall cycle time from tablets-in to results-out. All of these are important for developing lean testing processes.

The arrangement can improve overall quality of testing. The flow cell can be designed to be simple and reliable with on-board sensing to monitor its own performance without needing intrusive mechanical devices that can introduce cross contamination. The system may enable at-line testing on manufacturing lines and enable true statistical process control.

The invention claimed is:

1. An extraction system for distributing a test product in an extraction fluid, the system including:
    a flow cell having walls defining an internal passageway having an extraction region for holding the test product and having an upstream end and a downstream end between which the extraction region extends; and
    a pump having an inlet in fluid communication with the downstream end and an outlet in fluid communication with the upstream end, the pump being configured to re-circulate extraction fluid from the downstream end back to the upstream end so as to progressively erode the test product and distribute the test product in the extraction fluid
    wherein the upstream end has an internal cross-sectional area, the downstream end has an internal cross-sectional area, the internal cross-sectional area of the upstream end being larger than the internal cross-sectional area of the downstream end and the extraction region tapering from the upstream end to the downstream end;
    wherein the flow cell and the pump are connected and sealed so as to form a pressurized system; and
    wherein, for the extraction region, the walls defining the internal passageway have a shape defining a plurality of grooves side by side around the internal passageway, each one of the grooves extending at least partly from the upstream end to the downstream end.

2. An extraction system according to claim 1 wherein the extraction region is substantially conical.

3. An extraction system according to claim 2 wherein the included angle of the conical extraction region is substantially 55°.

4. An extraction system according to claim 1 wherein, adjacent to the upstream end, a first plurality of said grooves are provided and, adjacent the downstream end, a second plurality of said grooves are provided.

5. An extraction system according to claim 4 wherein said first plurality is greater than said second plurality.

6. An extraction system according to claim 4 wherein said first plurality is substantially 10.

7. An extraction system according to claim 4 wherein said second plurality is substantially 4.

8. An extraction system according to claim 1 wherein the flow cell has an internal volume between 5 ml and 100 ml.

9. An extraction system according to claim 1 wherein the internal cross-sectional area of the upstream end is substantially 500 mm$^2$.

10. An extraction system according to claim 1 wherein the internal cross-sectional area of the downstream end is substantially 3 mm$^2$.

11. An extraction system according to claim 1 further including, at a position downstream of the upstream end, a mesh element bridging the internal passageway so as to retain the test product.

12. An extraction system according to claim 11 wherein the mesh element is at a position between the upstream end and the downstream end.

13. An extraction system according to claim 4, further including, at a position downstream of the upstream end, a mesh element bridging the internal passageway so as to retain the test product, wherein the mesh element is at a position between the upstream end and the downstream end, and wherein the mesh element is at a position between the first plurality of grooves and the second plurality of groove.

14. An extraction system according to claim 11, wherein the mesh element is a mesh of substantially 0.3 mm mesh size.

15. An extraction system according to claim 1 further including an ultrasonic vibration generator configured to introduce ultrasonic vibrations to the flow cell.

16. An extraction system claim 1 further including an outlet valve providing fluid communication between the downstream end and selectively one of the inlet of the pump and a collection port from which fluid from the system can be collected.

17. An extraction system according to claim 16 further including a collection filter upstream of the collection port so as to provide a filtrate of the extraction fluid at the collection port.

18. An extraction system according to claim 1 further including a meter downstream of the downstream end configured to measure properties of the extraction fluid flowing from the downstream end and to output a corresponding signal.

19. An extraction system according to claim 18, wherein the meter includes one or both of a turbidity meter and a UV probe.

20. An extraction system according to claim 1 further including a controller configured to control the pump to pump extraction fluid under pressure from the downstream end to the upstream end so as to re-circulate extraction fluid.

21. An extraction system according to claim 20 further including a meter downstream of the downstream end configured to measure properties of the extraction fluid flowing from the downstream end and to output a corresponding signal, wherein the controller is configured to analyze the signal output from the meter and to determine from the analysis when the test product is fully distributed in the extraction fluid.

22. An extraction system according to claim 21 further including an outlet valve providing fluid communication between the downstream end and selectively one of the inlet of the pump and a collection port from which fluid from the system can be collected, wherein the controller is further configured to slow the pump and to control the outlet valve to connect the downstream end to the collection port when it is determined that the test product is fully distributed in the extraction fluid.

23. An extraction system according to claim 20, wherein the controller is further configured to reverse the direction of pumping of the pump when a blockage is determined.

24. An extraction system for distributing a test product in an extraction fluid, the system including:
 a flow cell having walls defining an internal passageway having an extraction region for holding the test product and having an upstream end and a downstream end between which the extraction region extends; and
 a pump having an inlet in fluid communication with the downstream end and an outlet in fluid communication with the upstream end, the pump being configured to re-circulate extraction fluid from the downstream end back to the upstream end so as to progressively erode the test product and distribute the test product in the extraction fluid;
 wherein the upstream end has an internal cross-sectional area, the downstream end has an internal cross-sectional area, the internal cross-sectional area of the upstream end being larger than the internal cross- sectional area of the downstream end and the extraction region tapering from the upstream end to the downstream end;
 wherein the flow cell and the pump are connected and sealed so as to form a pressurized system; and
 wherein, for the extraction region, the walls defining the internal passageway have a shape defining a plurality of grooves side by side around the internal passageway each one of the grooves extending in the axial direction of the tapered extraction region at least partly from the upstream end to the downstream end.

25. An extraction system for distributing a test product in an extraction fluid, the system including:
 a flow cell having walls defining an internal passageway having an extraction region for holding the test product and having an upstream end and a downstream end between which the extraction region extends; and
 a pump having an inlet in fluid communication with the downstream end and an outlet in fluid communication with the upstream end, the pump being configured to re-circulate extraction fluid from the downstream end back to the upstream end so as to progressively erode the test product and distribute the test product in the extraction fluid;
 wherein the upstream end has an internal cross-sectional area, the downstream end has an internal cross-sectional area, the internal cross-sectional area of the upstream end being larger than the internal cross- sectional area of the downstream end and the extraction region tapering from the upstream end to the downstream end;
 wherein the flow cell and the pump are connected and sealed so as to form a pressurized system and the pump is configured to positively pump the flow cell at pressures higher than 1 bar; and
 wherein, for the extraction region, the walls defining the internal passageway have a shape defining a plurality of grooves side by side around the internal passageway, each one of the grooves extending at least partly from the upstream end to the downstream end.

* * * * *